United States Patent
Vora et al.

[11] Patent Number: 6,025,533
[45] Date of Patent: Feb. 15, 2000

[54] OLIGOMER PRODUCTION WITH CATALYTIC DISTILLATION

[75] Inventors: Bipin V. Vora, Darien; Harold U. Hammershaimb, Western Springs, both of Ill.

[73] Assignee: UOP LLC, Des Plaines, Ill.

[21] Appl. No.: 09/058,607

[22] Filed: Apr. 10, 1998

[51] Int. Cl.$^7$ .................................................. C07C 2/08
[52] U.S. Cl. .................. 585/330; 585/329; 585/324; 585/315
[58] Field of Search .................. 585/330, 329, 585/315, 324

[56] References Cited

U.S. PATENT DOCUMENTS

| | | | |
|---|---|---|---|
| 2,526,966 | 10/1950 | Oberfell et al. | 196/1 |
| 4,304,948 | 12/1981 | Vora et al. | 585/315 |
| 4,393,259 | 7/1983 | Ward et al. | 585/315 |
| 4,678,645 | 7/1987 | Chang et al. | 422/190 |
| 4,749,820 | 6/1988 | Kuo et al. | 585/330 |
| 4,788,364 | 11/1988 | Harandi | 585/312 |
| 5,049,360 | 9/1991 | Harandi et al. | 422/141 |
| 5,395,981 | 3/1995 | Marker | 568/697 |
| 5,399,787 | 3/1995 | Ozmen et al. | 568/697 |
| 5,498,811 | 3/1996 | Perego et al. | 585/324 |
| 5,714,661 | 2/1998 | Tuli et al. | 585/533 |
| 5,811,608 | 9/1998 | Stine et al. | 585/316 |
| 5,847,252 | 12/1998 | Stine et al. | 585/330 |
| 5,856,604 | 1/1999 | Stine et al. | 585/310 |

FOREIGN PATENT DOCUMENTS 2186287A  8/1987  United Kingdom .

*Primary Examiner*—Walter D. Griffin
*Attorney, Agent, or Firm*—Thomas K. McBride; John G. Tolomei

[57] ABSTRACT

This process for the production of heavy oligomers by a combination of dehydrogenation and oligomerization uses a bed of saturation catalyst in a debutanizer to simplify the saturation and recycle of $C_4$ hydrocarbons to the dehydrogenation zone. The catalytic distillation zone is located in the top of the debutanizer column and may offer further efficiency improvements to the process when used in series with a bed of alkylation or oligomerization catalyst in the distillation zone. The bed of alkylation or oligomerization catalyst reduces the quantity of $C_4$ hydrocarbons recycled to the dehydrogenation zone by oligomerizing unconverted $C_4$ olefins in the distillation column. Conversion of $C_4$ olefins in the distillation column facilitates the operation of the oligomerization zone at lower conversion conditions that favor production of high octane products. The catalytic distillation arrangement is particularly beneficial in a combination for motor fuel from isoparaffins by dehydrogenation, oligomerization and saturation where the mass flow through the saturation zone is also reduced by alkylation and saturation in the distillation column.

21 Claims, 1 Drawing Sheet

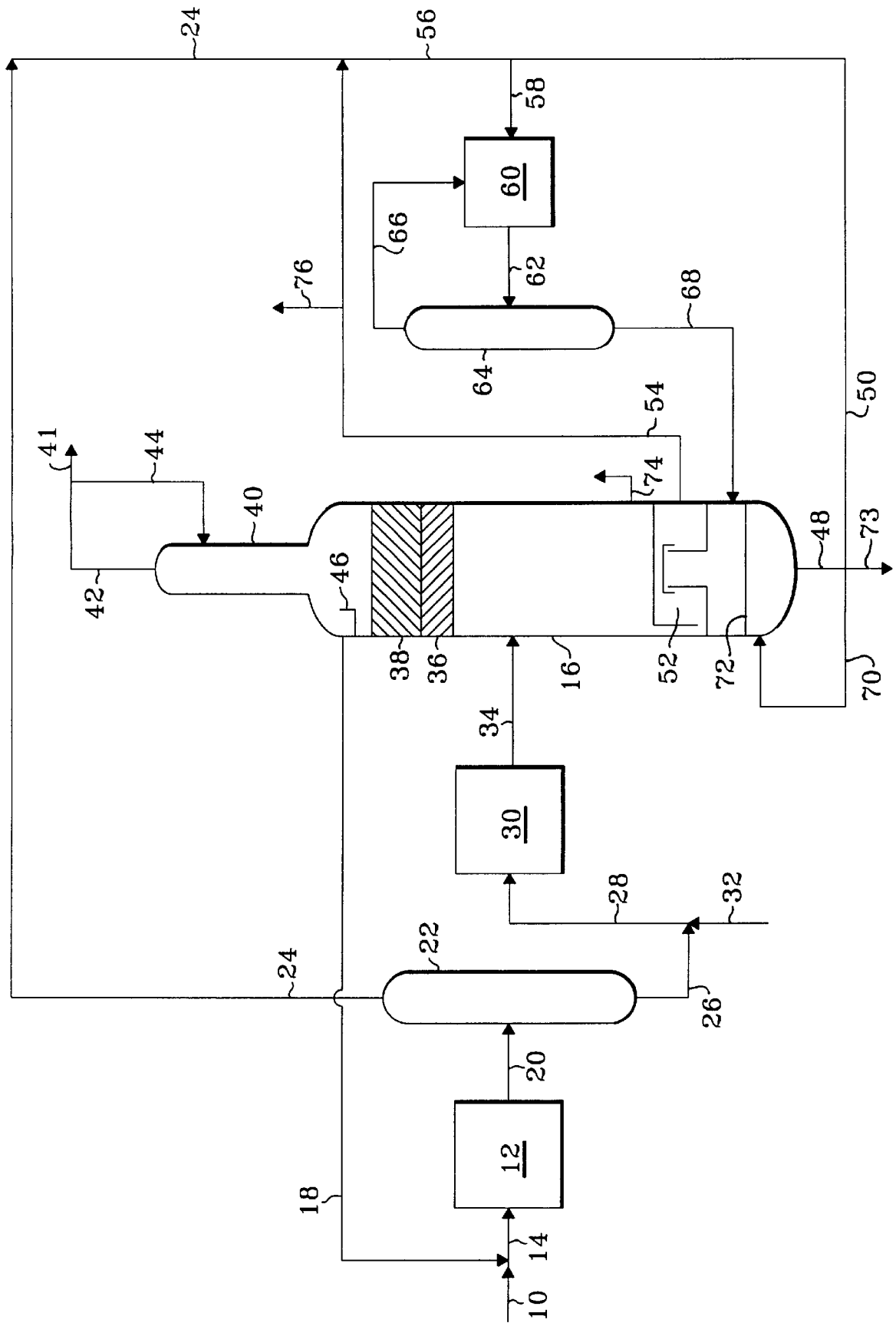

OLIGOMER PRODUCTION WITH CATALYTIC DISTILLATION

FIELD OF THE INVENTION

This invention relates generally to the production of oligomers from light paraffins and olefins by the dehydrogenation of light paraffins and the oligomerization of light olefins.

BACKGROUND OF THE INVENTION

Prior Art

A continuing demand exists for the conversion of isobutane and light olefins into high octane motor fuels. The term "HF alkylation commonly refers to the alkylation of isobutane with propylene, butenes and amylenes using a hydrofluoric acid (HF) catalyst. HF alkylation has provided a highly successful method for the production of high octane motor fuels. Despite a long history of safe operation, recent concerns over the possibility of a catastrophic release of HF acid from HF alkylation units has prompted the investigation of modifications or alternatives to the HF alkylation process for the production of motor fuels. One existing alternative is a similar alkylation process that uses sulfuric acid as the catalyst. While the use of sulfuric acid may decrease the degree of the hazard that some associate with the use of HF acid, sulfuric acid processes are still perceived as possibly presenting the same hazard and are not as economically advantageous as the HF alkylation process. Therefore, processing substitutes for the HF alkylation process are still sought.

Other methods of combining isobutane with light olefins to produce motor fuels are known and practiced. However, they do not produce the same quality gasoline products or they are more expensive to install and operate. One such alternative is the dehydrogenation of butanes and the oligomerization of the resulting olefins to produce gasoline boiling range hydrocarbons. The oligomerization of light olefins into higher molecular weight motor fuels using a solid phosphoric acid is well known and its use predates the HF alkylation process. Such oligomerization processes are also referred to as catalytic condensation and polymerization with the resulting motor fuel often referred to as polymer gasoline. Patents disclosing the dehydrogenation of a light paraffin stream with oligomerization of the dehydrogenation effluent include U.S. Pat. No. 4,393,259, U.S. Pat. No. 5,049,360, U.S. Pat. No. 4,749,820, U.S. Pat. No. 4,304,948 and U.S. Pat. No. 2,526,966.

It is also known to hydrotreat the olefinic hydrocarbon streams produced by oligomerization to saturate olefins. Patent GB 2186287 discloses dehydrogenation of a $C_4$ fraction and oligomerization of the resulting olefins to produce a jet aircraft fuel that is optionally hydrogenated to produce premium gasoline. The hydrotreatment of jet fuels, diesel fuels, and lubes produced by dehydrogenation and oligomerization of light paraffins is disclosed in U.S. Pat. No. 4,678,645. Hydrotreating is known to be particularly beneficial when saturating isooctenes to isooctane gasoline. However, hydrotreating is not beneficial for all gasoline fractions produced by oligomerization and can lower octane ratings.

Inefficiency in the production of gasoline boiling range hydrocarbons by the dehydrogenation of butanes stems from the interrelationship of the oligomerization reaction zone and the dehydrogenation zone. Operating the oligomerization zone at conditions that will maximize the conversion of $C_4$ olefins and other olefins degrades the octane quality of resulting oligomers. Maintaining conversion of the $C_4$ olefins that enter the oligomerization zone somewhere between 70% to 80% not only results in a high quality oligomerization product, but also a lot of unconverted $C_4$ olefins. These unconverted $C_4$ olefins are in addition to the butanes that are present in the feed to the oligomerization zone in proportions of 5 to 30 wt. %. The unconverted $C_4$ olefins are not readily separated from paraffins and are recycled together to the dehydrogenation zone after saturation of the entire stream to hydrogenate the unconverted olefins and to prevent the formation of diolefins in the dehydrogenation zone. The passage of additional large quantities of $C_4$ olefins through both the saturation and dehydrogenation zones reduces the efficiency of the dehydrogenation zones and increases the cost of operating an integrated process.

The reaction of olefins to produce ethers using catalytic distillation has been practiced.

Methods for catalytic distillation are disclosed in U.S. Pat. No. 5,399,787 issued to Ozmen et. al. and U.S. Pat. No. 5,395,981 issued to Marker.

It is an object of this invention to provide an efficient alternative to HF alkylation by reducing the amount of $C_4$ olefins that is recycled in the integration of a dehydrogenation zone and an oligomerization zone.

It is a further object of this invention to provide an integrated process for the combination of isobutane with light olefins that advantageously produces a comparable motor fuel product in a uniquely integrated series of dehydrogenation, oligomerization, and saturation steps.

BRIEF DESCRIPTION OF THE INVENTION

This invention adds catalytic distillation to the combination of a dehydrogenation zone and an oligomerization zone for the production of $C_7$ and heavier oligomers in manner that can be used to simplify the process flow scheme and to eliminate unnecessary mass flow through the dehydrogenation zone and oligomerization zone. The process adds at least one catalyst bed in the top of a distillation column for separating the oligomerization effluent of the dehydrogenation and oligomerization combination. The dehydrogenation zone supplies at least a portion of the mixture of $C_4$ paraffins and olefins to the oligomerization zone. The catalytic distillation zone saturates the unreacted $C_4$ olefins from the oligomerization zone, eliminates the need for a separate saturation zone, and allows the simple and efficient recovery of $C_4$ recycle stream directly from the distillation column that serves as the primary separator.

The invention is most beneficial when the distillation zone includes a second bed of oligomerization catalyst below the bed of saturation catalyst. The lower bed of oligomerization catalyst converts additional $C_4$ olefins with the unconverted paraffins from the dehydrogenation zone and reduces the total amount of $C_4$ recycle through both the dehydrogenation and oligomerization zones. Where the process passes the resulting heavy oligomers from the oligomerization zone through a saturation zone, the oligomerization and saturation zones within the column eliminate additional $C_4$ traffic through the column saturation zone. The oligomerization and saturation zones accomplish this by recovering the additional $C_4$'s that would pass through the column saturation zone or by reacting the $C_4$'s to heavier oligomers. By this method the integration of butane dehydrogenation with the oligomerization of the resulting isobutenes and hydrotreatment of the resulting oligomers is efficiently and simply completed to produce a motor fuel equivalent to that produced by HF alkylation.

In a broad embodiment, this invention is a process for the production of an oligomerization zone product from a feedstream comprising isobutane. The process passes a dehydrogenation feedstream comprising isobutane and a recycle stream comprising saturated $C_4$ hydrocarbons to a dehydrogenation zone and contacts the feedstream in the dehydrogenation zone with a dehydrogenation catalyst at dehydrogenation conditions to produce a dehydrogenation zone effluent comprising isobutene and hydrogen. At least a portion of the dehydrogenation zone effluent passes to an oligomerization zone to supply at least a portion of an oligomerization zone feed. The oligomerization zone contacts the feed with a solid oligomerization catalyst at oligomerization conditions including a temperature of 200° F. to 500° F., a pressure of 100 to 1500 psig, and an LHSV of 0.5 to 8 to recover an oligomerization effluent comprising $C_7$ and heavier oligomers and unconverted isobutene. At least a portion of the oligomerization zone effluent stream passes to a distillation column that separates $C_4$ and lighter hydrocarbons from the $C_7$ and heavier oligomers. $C_4$ and lighter hydrocarbons pass upwardly through the column and into contact with a bed of saturation catalyst in a column saturation zone to saturate the $C_4$ and lighter hydrocarbons and to produce the recycle stream comprising $C_4$ saturated hydrocarbons in an upper portion of the column. The saturated $C_4$ recycle stream from the column returns as recycle to the dehydrogenation zone. An oligomerized stream, withdrawn from a lower portion of the column, supplies a product stream of $C_7$ and heavier oligomers.

In a more specific embodiment, this invention is a process for the production of a motor fuel product from a first input stream containing isobutane and a second input stream comprising olefins. The process includes the steps of passing at least a portion of the first input stream comprising isobutane and a $C_4$ recycle stream to a dehydrogenation zone and contacting the feedstream in the dehydrogenation zone with a dehydrogenation catalyst at dehydrogenation conditions to produce a dehydrogenation zone effluent comprising isobutene and hydrogen; separating hydrogen from the dehydrogenation effluent to produce a first hydrogen stream and a separated dehydrogenation effluent; passing at least a portion of the separated dehydrogenation effluent and the second input stream to an oligomerization zone and contacting the separated dehydrogenation effluent and the second input stream with a solid oligomerization catalyst at oligomerization conditions including a temperature of 200° F. to 500° F., a pressure of 100 to 1500 psig, and an LHSV of 0.5 to 10 to recover an oligomerization effluent comprising $C_8$ and higher oligomers and recover unconverted isobutene; passing the oligomerization zone effluent stream to a distillation column and separating $C_4$ and lighter hydrocarbons from the $C_8$ and heavier oligomers; passing the $C_4$ and lighter hydrocarbons upwardly through the column and first into contact with a bed of oligomerization catalyst at oligomerization conditions to oligomerize $C_4$ olefins and produce $C_8$ and heavier hydrocarbons that pass downwardly from the bed of oligomerization catalyst; passing $C_4$ and lighter hydrocarbons from the bed of oligomerization catalyst upwardly in the column to a bed of saturation catalyst in a column saturation zone to saturate the $C_4$ and lighter hydrocarbons and to produce the $C_4$ recycle stream comprising saturated hydrocarbons in an upper portion of the column; recycling the saturated $C_4$ recycle stream from the column to the dehydrogenation zone; recovering an oligomerized stream comprising $C_8$ and heavier olefins from the distillation column and passing the oligomerized stream and the first hydrogen stream to a saturation zone and into contact with a saturation catalyst at saturation conditions to saturate olefins in the oligomerized stream and to produce a saturated stream; separating a second hydrogen stream from the saturated stream for return to the saturation zone and returning the remainder of the saturated stream to the distillation column; and, recovering a net bottoms stream comprising the motor fuel product from the distillation column.

Other objects, embodiments and details of this invention will be provided in the following detailed disclosure of the invention.

BRIEF DESCRIPTION OF THE DRAWINGS

The FIGURE is a schematic process flow diagram of the invention showing principal processing zones and the process flow between zones.

DETAILED DESCRIPTION OF THE INVENTION

The process and different operational steps will be described in conjunction with the figure. The figure shows only one form of the invention and only those portions of the process that are necessary to gain an understanding of the invention and of the necessary means of integrating the different process steps that comprise the invention. Further details related to valves, control means, pumps, compressors, coolers, and other necessary processing equipment are well known to those skilled in the art and are not described in detail unless necessary for an understanding of the invention.

The primary feed to the process unit comprises a first input stream containing isobutane that typically enters the process via a line 10 and passes to a dehydrogenation zone 12 via a line 14. Direct entry of the feed into the dehydrogenation zone is believed to offer the most advantageous location for the input of the primary feed, but the primary feed may enter the process at other locations. One alternate location for the primary feed would include direct entry into a primary separator 16. A line 18 returns an isobutane recycle stream from separator 16 to the dehydrogenation zone via line 14.

Dehydrogenation zone 12 at least partially dehydrogenates isobutane and other $C_4$ hydrocarbons in the feed to produce a dehydrogenation zone effluent that exits the dehydrogenation via line 20. The effluent from the dehydrogenation reaction zone contains at least hydrogen, butane, butenes, some light hydrocarbons, and small amounts of heavy hydrocarbons comprising mainly xylenes and aromatics. The dehydrogenation zone effluent usually enters a separator 22 for separation and recovery of hydrogen via a line 24. A portion of the hydrogen from the dehydrogenation zone of this invention may be recycled to the inlet of the dehydrogenation zone.

The remainder of the dehydrogenation zone effluent, which contains $C_4$ olefins and—in most cases—some lighter paraffins and olefins, passes from separator 22 via a line 26 and enters an oligomerization zone 30 via line a line 28. In addition to the olefins from line 26, a second input stream containing additional olefins may be sent to oligomerization zone 30 via a line 32. The olefins entering through line 32 will include normal butenes and isobutene and may also include $C_3$ and $C_5$ olefins as well as some paraffins. In addition to the olefin feed a heavy recycle stream comprising $C_8$ and heavier paraffins (not shown) may be combined with the feed to the oligomerization zone. In oligomerization zone 30 the oligomerization feed typically passes serially through a series of oligomerization reactors which are divided into multiple stages. A distribution system supplies quench to each stage via quench distribution lines. Oligomerization zone 30 contacts the feedstream with an oligomerization catalyst and oligomerizes the olefins into higher carbon products which will usually consist of $C_7$ and higher olefins depending on the variety of olefin species present in the entering feed.

A line 34 passes the oligomerization effluent, which contains $C_7$ and heavier olefins along with unconverted $C_4$ olefins and normally some light paraffins, to separator 16. Separator 16 is the main separator of the process and preferably comprises a multifunction distillation column that serves primarily as a debutanizer. Effluent from the oligomerization zone enters the column at an intermediate tray location (not shown). As the fractionation passes the $C_4$ and lighter hydrocarbons upwardly in the column, the lighter fraction eventually reaches a bed of saturation catalyst 38 and optionally a bed of oligomerization or alkylation catalyst 36. When present bed 36 functions as a catalytic distillation zone, it oligomerizes or alkylates $C_4$ olefins with the $C_4$ paraffins by contact with catalyst into higher boiling olefins that descend in the column. $C_4$ and lighter hydrocarbons that are not oligomerized or alkylated continue to pass upwardly into the bed of saturation catalyst 38 that saturates any ascending olefins. Butanes are withdrawn from above bed 38 for recycle to the dehydrogenation zone.

Typically, distillation of the saturated stream will continue in a rectification zone 40 located at the top of the column. Rectification zone 40 separates light ends that are taken overhead by line 42 which after removal of a reflux stream 44 provides a net gas stream that is removed from the process. The separated butanes, primarily isobutane, is preferably withdrawn from below the rectification zone via a sidedraw tray 46.

Any heavy oligomer product or alkylate produced by providing the bed 36 that contains oligomerization or alkylation catalyst passes downwardly in the column with the remainder of the descending heavy fraction from the oligomerization zone. A separated heavy fraction is removed from the column via bottoms stream 48. A portion of this bottoms stream 48 may supply heavy olefins to a saturation zone 60. Alternately, all or a portion of any heavy olefin-containing feed for saturation zone 60 may be withdrawn from an intermediate portion of the column at a tray location 50 via a line 54. Above tray 52 the separator 16 may provide an additional draw off point from a tray location selected to deliver a stream 74 that primarily consists of normal butane.

Heavy olefin-containing feed withdrawn via line 54 and/ or line 50 is combined with hydrogen from line 24 and enters the saturation reaction zone 60 via lines 56 and 58. Any outside make-up hydrogen needed for the process is charged to the saturation zone. The saturation zone saturates the unsaturated gasoline boiling range components from the oligomerization zone to provide an alkylate quality product stream. The saturation zone will typically use a plurality of reactors arranged in series with feed passing through each reactor. The series reactor arrangement permits greater control of temperatures. The preferred arrangement of the saturation zone will be a two stage hydrotreating reactor system. To control the temperature exotherm from the saturation reaction, a process quench stream may provide quenching between reactor stages or as an intermediate quench. A line 62 transfers the saturation zone effluent to a separator 64 that recovers an overhead stream of hydrogen via a line 66 for return to saturation zone 60.

A line 68 withdraws a heavy saturated stream from separator 64. Preferably the heavy saturated stream returns to the fractionation column above at least the lowest tray level 72. When tray 52 is present to provide sidestream 54, line 68 will return the saturated stream to the column at a point below tray 52 to reduce the recycle of saturated hydrocarbons to saturation zone 60. A line 73 withdraws net saturated products from column 16 after recycling of any reboiled fraction via line 70.

Another arrangement of this invention may recover olefin products directly from the distillation column 16. One such arrangement would directly recover an olefin products as a sidecut such as from side stream from line 54 via a line 76. Selection of the withdrawal point will determine the carbon number range of the olefin product stream. A particularly beneficial arrangement of this type will recover $C_7$–$C_{10}$ olefins for use in plasticizers. The bottoms stream will withdraw remaining $C_{11}$ and heavier olefins. In accordance with this alternative the distillation arrangement may be further simplified when only recovering olefin products by eliminating the saturation zone 60 and the separator 64.

The primary feed will typically comprise a refinery paraffin stream that contains at least 20 wt % isobutane. Preferred feeds are rich in $C_4$ paraffins and contain a high percentage of isobutane. (The term "rich" when used herein means a stream having a weight or volume percent content of at least 50% of the mentioned component while the term "relatively rich" means a stream having a higher concentration of the mentioned component than the feed from which it was derived.) Preferred feeds for this process are rich in isobutane and will more preferably have an isobutane concentration in a range of from 55 wt % to 99 wt %. Typical sources for this feedstream are field butanes, refinery $C_4$ saturate streams, effluents from butane isomerization, and butanes from gas recovery units. The isobutane stream can be obtained from refinery butane streams or other sources that will preferably provide a butane rich feed.

The main separator column of this invention can facilitate the use of relatively impure isobutane-containing streams by prefractionating higher and lower boiling hydrocarbons from the dehydrogenation zone feed in the primary fractionator. Thus, feeds containing isobutane with substantial quantities of other hydrocarbons can still provide acceptable feed sources.

The primary separator of this invention provides both a fractionation function for recovery of feedstreams, recycle, off-gas and product streams while also providing a catalyst function to simplify recycle of butane to the dehydrogenation zone. The highly integrated column of this invention operates in its simplest form as a debutanier.

The heavy oligomer-containing stream from the oligomerization zone enters the column at a sufficient distance below the bed of saturation catalyst and any bed of oligomerization catalyst to provide enough stages of separation to remove substantially all of the heavy oligomers from the butanes. The bed of saturation catalyst contains a saturation catalyst that is suitable for the typical upper column temperatures which usually range from about 150° F. to 400° F. (65° C. to 180° C).

The preferred arrangement of the primary fractionator is as a single deisobutanizer column. Integration of the deisobutanizer column into simultaneous feed and product separation allows the process to efficiently perform the necessary distillations for the successful operation of the process. Integration of multiple feed inputs and stream outputs on the deisobutanizer column promote separation efficiency by permitting matching of stream compositions with column locations in a manner that reduces the overall size of the debutanizer column. The debutanizer column design is preferably arranged to provide the isobutane in the recycle or a combined feed and recycle to the dehydrogenation zone via a sidecut stream. The upper section of the debutanizer column can be operated at high or low purity. The carry over of $C_3$ hydrocarbons with the dehydrogenation zone feedstream does not present a problem for the column operation. Propane carried over with the feed from the column undergoes dehydrogenation in the dehydrogenation zone with a subsequent increase in oligomerization product.

The isobutane-containing feed can contain a large proportion of normal butane. The primary fractionator can provide an additional sidecut stream for the recovery of a normal butane-containing stream. It may often be desirable to send this stream to a butane isomerization zone to obtain additional isobutane for input to the process. The isobutane-containing sidecut stream from the distillation column passes to the dehydrogenation reaction zone.

Many dehydrogenation zones are available for use in this invention. The dehydrogenation section may use any type of reactor that will dehydrogenate the isobutane to isobutene. Catalytic dehydrogenation is an established hydrocarbon conversion process employed in the petroleum processing industry for producing olefins from paraffinic feedstocks. The art of catalytic dehydrogenation is well known. Briefly, suitable dehydrogenation processes will admix a feedstock with a stream comprising hydrogen and will contact the feed with catalyst in a reaction zone. As previously stated the preferred feedstocks for the catalytic dehydrogenation of this invention predominately comprise isobutane and may also contain propane and pentanes. The catalytic dehydrogenation process will treat the substantially paraffinic hydrocarbons to thereby form olefinic hydrocarbon compounds. Suitable dehydrogenation zones for this process provide a low conversion of isobutane to isobutene with a relatively low rate of catalyst fouling. Depending on the composition of the dehydrogenation catalyst, a small amount of sulfur may also be maintained with the feed to prevent carbon formation on metallic surfaces of the reactors and heaters and to passivate the catalyst.

Any suitable dehydrogenation catalyst may be used in the process of the present invention. The particular dehydrogenation reactor configuration will depend on the performance characteristics of the catalyst and the reaction zone. Preferred dehydrogenation zones for this invention operate at low conversion conditions. The olefin yield from the dehydrogenation reactor will usually be in a range of 10 wt % to 50 wt % and will more typically be in a range of from 15 wt % to 30 wt %. Operating conditions within the dehydrogenation zone are also chosen to produce an olefin effluent stream having an isobutene to normal butene ratio of more than 1. Low conversion conditions within the dehydrogenation zone can extend the life of the dehydrogenation catalyst. Low conversion conditions will usually give the catalyst a cycle life of at least 4 days and more typically 6 days. Any suitable method such as a swing bed or continuous catalyst regeneration procedures can regenerate the catalyst.

A catalytic dehydrogenation reaction is normally effected in the presence of catalyst particles comprised of one or more Group VIII nobel metals (e.g., platinum, iridium, rhodium, palladium) combined with a porous carrier such as a refractory inorganic oxide. Generally, the preferred catalyst comprises a platinum group metal component and an alkali metal component with the porous carrier. The catalyst may also contain promoter metals which advantageously improve the performance of the catalyst. It is preferable that the porous carrier material of the dehydrogenation catalyst be an absorptive high surface area support having a surface area of about 25 $m^2/g$ to about 500 $m^2/g$. The porous carrier material should be relatively refractory to the conditions utilized in the reaction zone and may be chosen from those carrier materials which have traditionally been utilized in dual function hydrocarbon conversion catalysts. A porous carrier material may, therefore, be chosen from an activated carbon, coke or charcoal, silica or silica gel, clays and silicates including those synthetically prepared and naturally occurring which may, or may not be, acid-treated as for example, attapulgus clay, diatomaceous earth, kieselguhr, bauxite; refractory inorganic oxides such as alumina, titanium dioxide, zirconium dioxides, magnesia, silica alumina, alumina boria, crystalline alumina silicates such as naturally occurring or synthetically prepared mordenite or a combination of one or more of these materials or other zeolite materials. The preferred porous carrier material is a refractory inorganic oxide, with the best results being obtained with an alumina carrier material. Alumina is the most commonly used carrier. The preferred alumina materials are known as the gamma, eta and theta alumina with gamma and theta alumina giving the best results. The preferred catalyst will have a theta alumina carrier which is in the form of spherical particles. Particles having relatively small diameters on the order of about 1/16" are preferred, but the particles may be as large as 1/4".

Of the platinum group metals, which include palladium, rhodium, ruthenium, osmium or iridium, the use of platinum is preferred. The preferred platinum group component after platinum is palladium. The platinum group component may exist within the final catalyst composite as a compound such as an oxide, sulfide, halide, oxysulfide, etc., of an elemental metal or in combination with one or more other ingredients of the catalyst. It is believed that the best results are obtained when substantially all of the platinum group components exist in the elemental state. The platinum group components generally comprises from about 0.01 wt % to about 2 wt % of the final catalytic composite calculated on an elemental basis. It is preferred that the platinum content of the catalyst be between about 0.2 wt % and 1 wt %. The platinum group component may be incorporated into the catalyst composite in any suitable manner such as by coprecipitation or cogelation with the preferred carrier material or by ion-exchange or impregnation of the carrier material. The preferred method of preparing the catalyst normally involves the utilization of a water-soluble, decomposable compound of a platinum group metal to impregnate the calcined carrier material. For example, the platinum group component may be added to the support by commingling the support with an aqueous solution of chloroplatinum or chloropalladic acid. An acid such as hydrogen chloride is generally added to the impregnation solution to aid in the distribution of the platinum group component throughout the carrier material.

The preferred alkali metal is normally either potassium or lithium, depending on the feed hydrocarbon. The concentration of the alkali metal may range from about 0.1 wt % to 3.5 wt %, but is preferably between 0.2 wt % and about 2.5 wt % calculated on an elemental basis. This component may be added to the catalyst by the methods described above as a separate step or simultaneously with the solution of another component.

As noted previously, the dehydrogenation catalyst may also contain a promoter metal. One such preferred promoter metal is tin. The tin component should constitute about 0.01 wt % to about 1 wt % tin. It is preferred that the atomic ratio of tin to platinum be between 1:1 and about 6:1. The tin component may be incorporated into the catalytic composite in any suitable manner known to effectively disperse this component in a very uniform manner throughout the carrier material. A preferred method of incorporating the tin component involves coprecipitation during the preparation of the preferred carrier material. This method typically involves the addition of a suitable, soluble tin compound such as stannous or stannic chloride to an alumina hydrosol, mixing these ingredients to obtain a uniform distribution throughout the sol, and then combining the hydrosol with a suitable gelling agent and dropping the resultant admixture into an oil bath. The tin component may also be added through the utilization of a soluble decomposable compound of tin to impregnate the calcined porous carrier material. A more detailed description of the preparation of the carrier material and the addition of platinum component and the tin component to the carrier material may be obtained by reference to U.S. Pat. No. 3,745,112.

Preferred dehydrogenation reaction zones for this invention beneficially integrate the dehydrogenation zone with the oligomerization reaction zone by the use of high pressure and low conversion conditions. The higher pressure and lower conversion will reduce catalyst deactivation and allow most dehydrogenation reaction zones to operate with reduced regeneration requirements. In addition higher pressure conditions in particular reduce compression requirements for effluent separation and improve process efficiency. The lower severity dehydrogenation zone reaction conditions can also provide the unreacted mass flow of butane for temperature control necessary for the condensation reactions. The low severity operation of the preferred dehydrogenation zones will result in an extended catalyst life.

Depending on the catalyst system and the properties of the dehydrogenation zone feed, the dehydrogenation reaction zone will use a solid catalyst that can operate as a fixed bed, a semi-regenerated bed or a continuous catalyst regeneration. The actual arrangement of the dehydrogenation zone may be relatively simple and include a single reactor and single heater. Moreover, the dehydrogenation catalytic reaction zone may consist of multiple catalyst beds. In one such system, the catalyst is employed within an annular bed through which it is movable via gravity flow.

During the course of a dehydrogenation reaction, catalyst particles become deactivated as a result of mechanisms such as the deposition of coke on the particles; that is, after a period of time in use, the ability of catalyst particles to promote dehydrogenation reactions decreases to the point that the catalyst is no longer useful. The catalyst must be reconditioned, or regenerated, before it can be reused in a dehydrogenation process.

In such systems, it is common practice to remove catalyst from the bottom of the reaction zone, regenerate it and then return it to the top of the reaction zone. Preferred methods of dehydrogenating light hydrocarbons, suitable for the continuous dehydrogenation of isobutane using a continuous catalyst regeneration system are described in U.S. Pat. Nos. 5,227,566; 3,978,150; 3,856,662; 3,854,887; 3,839,197; 3,825,116; and 3,706,536, the contents of which are hereby incorporated by reference.

In preferred form, the dehydrogenation process will employ a moving bed reaction zone and regeneration zone. Moving bed systems advantageously maintain production while the catalyst is removed or replaced. In a typical moving bed reaction zone, fresh catalyst particles are fed through the reaction zones by gravity. Catalyst is withdrawn from the bottom of the reaction zone and transported to a regeneration zone where a hereinafter described multi-step regeneration process is used to recondition the catalyst to restore its full reaction promoting ability. Catalyst flows by gravity through the various regeneration steps and then is withdrawn from the regeneration zone and furnished to the reaction zone. Movement of catalyst through the zones is often referred to as "continuous" though, in practice, it is "semi-continuous". "Semi-continuous" movement means the repeated transfer of relatively small amounts of catalyst at closely spaced points in time. For example, one batch per minute may be withdrawn from the bottom of a reaction zone and withdrawal may take one-half minute, that is, catalyst will flow for one-half minute. If the inventory in the reaction zone is large, the catalyst bed may be considered to be continuously moving.

In the preferred regeneration method for the dehydrogenation process of this invention, catalyst is contacted with a hot oxygen-containing gas stream (known as recycle gas) in order to remove coke which accumulates on surfaces of the catalyst while it is in a dehydrogenation reaction zone. Coke is comprised primarily of carbon, but it is also comprised of a relatively small quantity of hydrogen. The mechanism of coke removal is oxidation to carbon monoxide, carbon dioxide, and water. Coke content of spent catalyst may be as much as 20% of the catalyst weight, but 5–7% is a more typical amount. Within the combustion zone, coke is usually oxidized at temperatures ranging from about 850° F. (471° C.) to about 1000° F. (538° C.), but temperatures in localized regions may reach 1100° F. (593° C.) or more.

Oxygen for the combustion of coke typically enters what is called a combustion section of the regeneration zone in what has been termed a recycle gas. The recycle gas contains a low concentration of oxygen usually on the order of 0.5% to 1.5% by volume. The remainder of the recycle gas is usually composed of mainly inert combustion by-products. A system of blowers, heaters, and coolers maintain circulation and the temperature of the recycle gas in a recycle loop. A small quantity of the recycle gas stream is vented and replaced with a make-up stream of air or other oxygen-containing gas to maintain the dilute oxygen concentration in the recycle gas stream. The low oxygen level is maintained for temperature control.

It is also possible to use steam as a diluent for the combustion gas stream and to avoid the circulation of recycle gas. The preferred, low severity conversion conditions within the dehydrogenation zone result in a low coke load on the regeneration zone. The low coke loading requires only a small regeneration zone to provide sufficient coke combustion. Relatively small amounts of steam can be used to dilute an oxygen-containing stream to sufficiently low $O_2$ levels for a controlled heat release in the regeneration zone. Instead of air, a relatively pure oxygen stream may be preferred for admixture with the steam. The use of the preferred theta alumina catalyst will also provide the necessary resistance to hydrothermal deactivation of the catalyst for repeated regenerations with the steam diluent.

In addition to combustion, the regeneration normally includes steps of drying and redispersion. The catalyst particles can pass directly from the combustion zone directly into a drying zone where the water that is left on the catalyst particles after the combustion process is removed. Water is evaporated from the surface and pores of the catalyst particles by contact with a heated gas stream. Exposure to reactants in a wet reduction zone and the exposure to high temperatures and steam in the combustion zone serves to agglomerate the platinum on the surface of the catalyst.

Once the coke has been removed and the catalyst particles are in various states of oxidation, contact of the catalyst at a temperature between about 800° F. (426° C.) and 1100° F. (593° C.) in a chlorine environment will redisperse the platinum over the surface of the catalyst support. The arrangement of typical combustion, drying, and redispersion sections may be seen in U.S. Pat. Nos. 3,653,231 and 5,227,566; the contents of which are hereby incorporated by reference.

Operating conditions for the preferred low conversion dehydrogenation zone of this invention will usually include an operating temperature in the range of from 950° F. to 1200° F. with an operating temperature of at least 1100° F. being preferred and with an operating temperature of about 1130° F. being particularly preferred. A relatively high operating pressure characterizes the low conversion conditions of the preferred dehydrogenation zone and is usually within a range of 30 psig to 150 psig. Pressures for the preferred dehydrogenation zone are more typically at least 50 psig with pressures of about 70 psig to 110 psig being particularly preferred. Low conversion conditions will also permit the operation of the dehydrogenation zone at low hydrogen to hydrocarbon ratios in a range of from 0.1 to 4 and more preferably about 0.2. Space velocities for the dehydrogenation zone range from 0.5 to 50 and will normally exceed 10 and typically equal about 15. Further extension of the catalyst life from the typical 4 to 6 days may be obtained by operating with lower space velocities.

Most typical multireactor arrangements for the dehydrogenation zone will have interstage heating between reactors that establish adiabatic conditions through the reactors. Further improvements in catalyst life and reactor stability may be obtained by operating the reactor isothermally or with an ascending temperature profile over the reactant path of the reactor. Isothermal conditions or ascending temperature profiles may be established by indirect heat exchange between the reactants or catalyst beds within the reaction zone and by a circulating heat exchange medium. Such reactor arrangements can include internal heating means within the catalyst bed. Useful arrangements for internal heating of reactants can employ tubes or channels for indirect heating with catalyst and reactants on one side of a heat exchange surface and a heating medium on the opposite side. Other heating arrangements for the reactor bed may integrate a fired heater wherein catalyst is contained within tubes that occupy the combustion chamber of heater.

Low conversion and lower temperatures for the dehydrogenation reaction zone also promote savings in equipment. For example, a reciprocating compressor may be used in the recovery of recycle hydrogen from the dehydrogenation effluent. Higher pressures within the dehydrogenation zone and its integration with the saturation reaction zone also reduces the equipment expense associated with hydrogen supply and recovery. The relatively high pressures within the dehydrogenation zone can minimize cooling for the recovery of a hydrogen stream having purities of 80% or greater. The low conversion operation of the dehydrogenation zone allows utilization of such a low purity hydrogen stream due to the high amount of isobutane recycle that dilutes the harmful effect of any olefin carryover to the dehydrogenation zone. In addition, the supply of the excess hydrogen from the dehydrogenation zone to the saturation zone results in the recovery of excess $IC_4$ material in the primary fractionator which would otherwise pose an unacceptable loss of hydrocarbons in the operation of the process.

The effluent from the dehydrogenation will normally undergo recovery of hydrogen and removal of aromatics that are produced as the by-products from the preferred dehydrogenation process. Apart from heat exchange and pressurization all remaining portions of the dehydrogenation zone effluent will preferably pass directly to the oligomerization zone.

The feed to the oligomerization zone may consist solely of the effluent or effluent fraction from the dehydrogenation zone or may include the addition of a second input stream that contains olefins. The addition of second olefin feed downstream of the dehydrogenation zone separator can improve the efficient and advantageous performance of this process. The source of the second olefin input stream is typically a light gas stream recovered from the gas separation section of an FCC process. Other sources for suitable secondary olefin feeds will also include $C_4$ streams from steam cracking and coker off-gas. The second olefin feed stream is characterized by having an overall $C_4$ olefin concentration of at least 10 wt %. In most operations, this olefin feed stream will contain $C_4$ olefins, but it may also constitute all or substantial quantities of $C_3$ olefins. Typically, the olefin feeds can have a $C_3$ to $C_5$ olefin concentration of at least 30 wt %. Preferred feeds will have a $C_4$ olefin concentration of at least 30 wt % and more preferably have at least 50 wt %. Preferably the olefin feed stream will comprise at least 20 wt % and more preferably comprise 30 wt % isobutene. The isobutene will preferably comprise at least 33% of the total butenes. The olefin content of preferred feeds will predominately comprise branched olefins with isobutene present in large quantities. The second olefin stream may comprise at least 20 wt % normal butenes. The reaction of normal pentenes and propylene is promoted by maintaining a high concentration of isobutene in the feed to the oligomerization zone of this invention. Oligomerization of pentene and propylene into high octane isomers is promoted by having an olefin distribution in the feed to the isomerization zone that comprises at least 50 wt % isobutene. When large quantities of propylene are present in the feed to the oligomerization zone, the octane number of the product may be increased by raising the percentage of isobutene in the butene fraction of the feed. Preferably the butene fraction will comprise 65% isobutene when large amounts of propylene enter the oligomerization zone.

Suitable oligomerization zones for this invention take on many forms. The oligomerization process is known by many names such as catalytic condensation and also catalytic polymerization. Known catalysts for effecting such reactions include heterogenous catalysts such as Y zeolites, beta zeolites, silicalite, and sulfonated resins as well as homogenous catalysts such as borontrifluoride as described in U.S. Pat. Nos. 3,906,053, 3,916,019 and 3,981,941.

The preferred catalyst for the oligomerization process is a solid phosphoric acid (SPA) catalyst. As previously mentioned, the SPA catalyst refers to a solid catalyst that contains as a principal ingredient an acid of phosphorous such as ortho -pyro- or tetraphosphoric acid. The catalyst is normally formed by mixing the acid of phosphorous with a siliceous solid carrier to form a wet paste. This wet paste may be calcined and then crushed to yield catalyst particles where the paste may be extruded or pelleted prior to calcining to produce more uniform catalyst particles. The carrier is preferably a naturally occurring porous silica-containing material such as kieselguhr, kaolin, infusorial earth, and diatomaceous earth. A minor amount of various additives such as mineral talc, fuller's earth, and iron compounds including iron oxide may be added to the carrier to increase its strength and hardness. The combination of the carrier and the additives preferably comprises about 15–30% of the catalyst, with the remainder being the phosphoric acid. The additive may comprise about 3–20% of the total carrier material. However, variations from this such as a lower phosphoric acid content are possible. Further details as to the composition and production of SPA catalysts may be obtained from U.S. Pat. Nos. 3,050,472; 3,050,473, and 3,132,109 and from other references.

Oligomerization zones in general are maintained at conditions which may vary widely due to the previously listed variables. In this invention the oligomerization reaction zone is preferably operated at temperatures and pressures that increase compatibility with the dehydrogenation reaction zone effluent and the feed of the oligomerization reaction zone to the saturation reaction zone. A broad range of suitable pressures is from about 15 psig to about 1200 psig. The recycle of $C_8$ and heavier paraffins from the saturation zone has been found in some cases to improve the selectivity of the oligomerization reaction zone to $C_8$ olefin production.

In the preferred embodiment, an SPA catalyst is utilized in a chamber-type reactor to form an effluent containing, in addition to unreacted $C_4$ hydrocarbons, principally $C_5$ through $C_{12}$ hydrocarbons with a large amount of $C_8$ and $C_{12}$ dimers and trimers having boiling points within a gasoline boiling point range of about 100° F. to about 450° F. as determined by the appropriate ASTM distillation method. The preferred operating temperature of the oligomerization reaction zone will typically be in a range of from 200° F. to 500° F. and will more typically be in a range of from 300° F. to 450° F. Pressures within the oligomerization reaction zone will usually be in a range of from 200 psig to 1200 psig and more typically in a range of from 200 psig to 600 psig. Steam or water may be fed into the reactor to maintain the desired water content in the preferred catalyst.

The catalyst is preferably disposed in fixed beds within the oligomerization zone in what is known as a chamber-type reactor structure. In a chamber-type reactor, the reactants flow through a series of large diameter catalyst beds. The temperature of the reactants can be controlled by recycling relatively inert hydrocarbons which act as a heat sink. Unreacted isobutane from the dehydrogenation zone supplies a large proportion of the inert hydrocarbons that act as the heat sink. Temperature control within the oligomerization reaction zone is also promoted by the use of a quench material. A quench material that comprises the inert materials and heavy product material from the saturation zone may be used simultaneously for temperature control. The quench material serves as its primary advantage, the control of temperatures within the oligomerization reaction zone. As a secondary purpose, the quench material can provide a flushing function to inhibit the development of coke and the deactivation of the catalyst within the reaction zones. As pressure within the oligomerization reaction zone decreases, the flushing function of the quench material decreases as the vaporization of the reactants and quench within the reaction zone increase. The use of higher molecular weight quench material within the oligomerization reaction zones to inhibit coking while permitting lower pressure operation is one possible method for the operation of this invention. Thus, the addition of heavier quench materials facilitates the operation of the oligomerization zone at higher temperatures and lower pressures while still flushing the catalyst and preventing coke production. The recycle of higher molecular weight paraffins, such as $C_8$ and heavier hydrocarbons from the saturation effluent, can also improve selectivity of the oligomerization zone to produce the desired $C_7^+$ olefin products. Since the higher molecular weight materials have benefits beyond use as a quench, it can be beneficial to add all or a portion of such material to the inlet of oligomerization reactor with the feed.

The different catalyst beds are preferably contained within one or more cylindrical, vertically oriented vessels and the feed stream preferably enters the top of the reactor. Typically, a chamber-type reactor will contain about five catalyst beds.

Depending on the addition of any secondary olefin input stream, the combined feed to the oligomerization zone will preferably have a ratio of paraffins to olefins of from 1:1 to 5:1. Typically, the paraffin concentration of the feed to the oligomerization reaction zone will be at least 50 wt % and more typically will be at least 65 wt %. A high percentage of the olefins in the feed stream entering the process as the secondary feed stream upstream can be reacted in the oligomerization reaction zone along with the isobutene to produce olefin conversions in the range of from 80% to 99%. The principal oligomerization products comprise $C_7^+$ olefins.

The oligomerization effluent, containing principally isobutane and the olefinic gasoline components, passes to a distillation column that contains catalyst beds for catalytic distillation and vapor liquid contacting trays for distillation. The catalytic distillation sections are located in an upper section of the column above the entry point of the oligomerization effluent stream. A minimum of approximately 5 tray levels are provided between the oligomerization effluent entry point and the first catalyst bed to provide an initial separation of heavy oligomers. The number of tray levels between the first catalyst bed and the oligomerization effluent entry point remains relatively constant in the presence, or absence, of the alkylation/oligomerization catalyst bed. Catalyst for the saturation of $C_4$ olefins is located directly above any alkylation/oligomerization catalyst. Contact of the oligomerized hydrocarbons with alkylation catalyst in the distillation zone is avoided to prevent further alkylation/oligomerization and the production of unwanted heavy hydrocarbons. Additional heat generation by saturation and/or alkylation/oligomerization of olefins in the upper section of the distillation column is not beneficial to the catalyst distillation operation. Catalyst may be retained in the catalyst beds in a variety of trays configurations or packing arrangements that are known for retaining catalyst in catalytic distillation applications. A particularly preferred packing arrangement for retaining catalyst in catalytic distillation column is taught in U.S. Pat. No. 5,073,256 issued to A.P. Gelbein.

The size of the catalyst zones in the alkylation/oligomerization reactor will depend on whether there is a single saturation zone present or whether an alkylation/oligomerization zone is also present. The presence of the alkylation/oligomerization catalyst bed will serve to reduce the required size of the saturation catalyst by converting $C_4$ olefins before they pass upwardly in the distillation column. The bed of saturation catalyst is sized to provide a complete saturation of all olefins that are withdrawn from the column as recycle to the dehydrogenation zone. The carryover of light gases from the oligomerization zone effluent and, when present, the external saturation zone will provide the necessary hydrogen for the saturation of olefins in the distillation column. Any size alkylation/oligomerization zone will benefit the process by reducing the amount of $C_4$ traffic through the column and dehydrogenation zone and by reducing the amount of $C_4$'s that require saturation. When provided, the alkylation/oligomerization catalyst bed will contain enough catalyst to provide at least a 50% conversion of all butenes that pass through the upper portion of the column and more preferably at least 80% conversion.

The saturation section of the column requires a catalyst that can operate at the relatively mild conditions at the upper end of the debutanizer column. Catalytic compositions that can be used in this process include combinations of clay and alumina-containing metallic elements from Group VIII alone and from both Group VIII and Group VIB of the Periodic Table have been found to be particularly useful. Group VIII elements include iron, cobalt, nickel, ruthenium, rhenium, palladium, osmium, indium and platinum, with palladium, cobalt, and nickel being particularly preferred. The Group VIB metals consist of chromium, molybdenum and tungsten, with molybdenum and tungsten being particularly preferred. The metallic components are supported on a porous carrier material. The carrier material may comprise alumina, clay or silica. Particularly useful catalysts are those containing palladium in the range of 0.2 wt % to 2 wt %. The weight percentages of the metals are calculated as though they existed in the metallic state. Other useful catalyst compositions contain 15 wt. % to 20 wt. % nickel on alumina or a combination of cobalt or nickel metals ranging from 2.0 to 5 wt % and from 5 to 15 wt % molybdenum on an alumina support. Typical commercial catalysts comprise spherical or extruded alumina based composites impregnated with Co—Mo or Ni—Mo in the proportions suggested above. The ABD of commercial catalysts generally range from 0.5 g/cc to 0.9 g/cc with surface areas ranging from 150 $m^2/g$ to 250 $m^2/g$. Generally, the higher the metals content on the catalyst, the more active the catalyst.

When provided, the alkylation/oligomerization zone can use any solid catalyst with enough alkylation/oligomerization activity at the conditions within the distillation column to significantly reduce the amount of $C_4$ olefins passing upwardly in the column. The previously mentioned oligomerization catalysts can be used in any column oligomerization zone. A wide variety of suitable solid alkylation catalysts are available. Examples of the suitable catalyst include sulfated alumina, beta zeolite, Y zeolite, or ion exchange resins.

The alkylation/oligomerization zone provides a catalytic distillation function as the lighter components of the alkylation/oligomerization zone rise upwardly and the olefinic components are reacted by contact with the alkylation/oligomerization zone. Fractionation of the components takes place as the resulting heavier alkylate material of oligomers descend downwardly and exit the bottom of the bed.

Remaining light paraffins and olefins continue to rise upwardly into contact with the saturation bed which saturates the rising hydrocarbons without performing significant further fractionation. The column is preferably arranged with a an upper rectification section that further separates light gases so that an overhead stream comprising $C_3$ and lighter hydrocarbons can be removed from the overhead of the column and the $C_4$ recycle can be withdrawn as liquid sidedraw.

Alkylate or oligomers produced within the column descend through the column and continue fractionation together with the oligomers that enter the column with the oligomerization effluent. A portion of the oligomers or the heavy column bottoms stream provides a reboiled stream to the column. A net oligomerization stream essentially free of all lighter hydrocarbon components can be recovered from the bottom of the column. The effluent from the distillation column zone will contain heavier hydrocarbons having at least 7 carbon atoms although some $C_5$ and $C_6$ hydrocarbons may be present. For most operations, the effluent will mainly contain $C_8$ and heavier hydrocarbons. In most cases, at least a portion of the oligomers recovered in the column undergo saturation in an integrated saturation zone.

Suitable saturation reactors will provide an essentially complete saturation of all olefins from the distillation column. As shown in the Figure, the feed to the saturation zone can be simply a portion of the column bottom stream. However, it is preferred to withdraw the feed to the saturation zone as a lower intermediate stream from a lower tray level of the column. Effluent from the saturation zone normally reenters the distillation column above the last tray location to remove lighter materials such as $C_4$-hydrocarbons that may reenter the column with the saturation zone effluent. The saturation zone feed is typically withdrawn from the column at a temperature in a range of from 200° F. to 350° F. and a pressure in a range of from 70 psig to 120 psig. The withdrawal point for the preferred lower intermediate stream is above the location to which the saturation zone effluent is returned. Returning the saturation zone effluent below the saturation withdrawal point reduces the recycle of saturates through the saturation column by increasing the concentration of oligomers in the feed to the saturation zone. The saturation zone will typically operate at higher temperatures than the oligomerization zone so that recovery of the feed from a lower end of the distillation column will provide additional quench materials and paraffins in the effluent from the oligomerization zone and will supply additional heat sink material for the higher operating temperatures of the saturation reaction zone.

Before entering the saturation zone the saturation feed from the distillation column is first mixed with a hydrogen-containing gas stream. The gas stream should contain at least 50 wt % of hydrogen. Preferably, the hydrogen-containing gas stream will have a hydrogen concentration greater than 75 wt % hydrogen. Hydrogen recovered from the dehydrogenation section supplies a major amount of the hydrogen input for the saturation zone with the remainder of the necessary hydrogen supplied from outside sources such as a make-up hydrogen stream. High purity is preferred for the make-up hydrogen to increase the overall purity of the hydrogen entering the saturation zone thereby reducing the volume of light hydrocarbons. These light hydrocarbons are undesirable since their presence needlessly increases the mass volume through the saturation reaction zone and their relatively high vapor pressure can increase the loss of isobutane in the deisobutanizer column.

Hydrogen is mixed with the saturation feed from the distillation column in proportions that will produce a hydrogen to hydrocarbon ratio in a range of 0.1 to 2. and more preferably in a range of from 0.15 to 0.30. Preferably the saturation zone of this invention will comprise a hydrotreater section that requires a hydrogen to hydrocarbon ratio of not more than 0.9 stdm$^3$/m$^3$ (50 SCFB) at the effluent of the saturation reactor.

The preferred saturation reactor of this invention will provide an essentially complete saturation of all unsaturated hydrocarbons. Conditions within the hydrotreating zone typically include a temperature in the range of 200° F.–600° F., a pressure of from 100 psig to 1000 psig and a liquid hourly space velocity of from 1 to 20. Preferably, the reaction conditions are selected to keep the hydrocarbon feed in a vapor phase. The hydrotreater arrangement will generally operate at temperatures that permit the raising of the combined feed stream to reaction temperatures by heat exchange with hydrotreater effluent.

The preferred hydrotreatment reactor contains a fixed bed of hydrotreatment catalyst. Catalytic compositions that can be used in this process include traditional hydrotreating catalysts. Combinations of clay and alumina-containing metallic elements from Group VIII alone and from both Group VIII and Group VIB of the Periodic Table have been found to be particularly useful. Group VIII elements include iron, cobalt, nickel, ruthenium, rhenium, palladium, osmium, indium and platinum, with cobalt and nickel being particularly preferred. The Group VIB metals consist of chromium, molybdenum and tungsten, with molybdenum and tungsten being particularly preferred. The metallic components are supported on a porous carrier material. The carrier material may comprise alumina, clay or silica. Particularly useful catalysts are those containing a combination of cobalt or nickel metals ranging from 2.0 wt % to 5 wt % and from 5 wt % to 15 wt % molybdenum on an alumina support. The weight percentages of the metals are calculated as though they existed in the metallic state. Typical commercial catalysts comprise spherical or extruded alumina based composites impregnated with Co—Mo or Ni—Mo in the proportions suggested above. Other useful catalyst compositions contain 15 wt. % to 20 wt. % nickel on alumina. The ABD of commercial catalysts generally range from 0.5 g/cc to 0.9 g/cc with surface areas ranging from 150 m$^2$/g to 250 m$^2$/g. Generally, the higher the metals content on the catalyst, the more active the catalyst. Effluent from the saturation reaction zone typically enters a quench separator for recovery and recycle of hydrogen to the saturation reaction zone.

EXAMPLE 1

In order to show the oligomerization of $C_4$ hydrocarbons in a distillation column, a feed comprising 0.1 wt % propane, 65.8 wt %, isobutane, 0.5 wt % normal butane, 16.6 wt % 1-butene, 10.8 wt % trans 2-butene and 6.2 wt % cis 2-butene is charged to a catalyst zone in a distillation column at a rate of 100 grams/hour. The catalyst zone contains a 50-50 mix of a zirconium sulfate and alpha alumina catalyst. The catalyst bed operates at temperatures in a range of from 100° F. to 175° F. and pressure of from 120 psig to 240 psig. After 190 hours of operation and at catalyst temperatures of about 175° F. and pressure of about 240 psig, the conversions of 1-butene is above 98% and the conversion of cis and trans 2-butene is in the range of from 94% to 98%. Following the separation of the butanes, the product has the molecular weight distribution as given in Table 1.

TABLE 1

MOLECULAR WEIGHT DISTRIBUTION
(ISOBUTANE FREE BASIS)

| | | |
|---|---|---|
| C5–C8 | = | 45% |
| C9–C12 | = | 33.8% |
| C13–C16 | = | 16.3% |
| C20 | = | 3.9% |
| C24 | = | 1% |

EXAMPLE 2

To more fully demonstrate the attendant advantages of the present invention, the following example is based on thermodynamic analysis and engineering calculations. The example presents the operation of the invention as depicted in the Figure and reference numbers used in this example refer to this Figure. As with the Figure, details such as miscellaneous pumps, heaters, coolers, valving, start-up lines and similar hardware have been omitted as being non-essential to a clear understanding of the techniques involved.

A feed input stream containing about 97 mol % isobutane, 2 mol % normal butane, and 1 mol % propane enters the process via line 10. A recycle stream 18 containing products and having the composition given in Table 2 is combined with the input stream to provide a dehydrogenation zone input stream. The isobutane feedstream for the dehydrogenation zone is combined with the sulfur from line 17 to produce a concentration of 25 ppm sulfur in the feed. Hydrogen from the dehydrogenation zone is internally recycled to provide any necessary hydrogen input. The dehydrogenation input stream enters the dehydrogenation zone 12 at a temperature of 1150° F. and a pressure of 30–50 psig. The feedstream passes through two stages of dehydrogenation where it contacts a dehydrogenation zone catalyst. The combined feed passes through the dehydrogenation zone at a LHSV of about 15.

TABLE 2

| Stream | 18 | 32 | 34 | 41 | 68 | 74 |
|---|---|---|---|---|---|---|
| Mole % | | | | | | |
| $H_2$ | 0.00 | 0.00 | 1.80 | 10.75 | 0.37 | 0.01 |
| $C_1$ | 0.08 | 0.00 | 0.52 | 45.92 | 0.10 | 0.01 |
| $C_2$ | 0.17 | 0.00 | 0.29 | 5.82 | 0.06 | 0.01 |
| $C_3$ | 7.33 | 0.37 | 6.10 | 29.74 | 0.10 | 0.02 |
| $C_3=$ | 0.00 | 0.02 | 0.16 | 0.00 | 0.00 | 0.00 |
| $IC_4$ | 89.49 | 32.89 | 62.11 | 7.42 | 3.13 | 10.62 |
| $IC_4=$ | 0.00 | 15.53 | 2.75 | 0.36 | 0.00 | 0.00 |
| $NC_4$ | 2.94 | 11.01 | 5.21 | 0.00 | 29.09 | 89.33 |
| $1\text{-}NC_4=$ | 0.00 | 13.23 | 1.87 | 0.00 | 0.00 | 0.00 |
| $C2\text{-}NC_4=$ | 0.00 | 10.24 | 1.48 | 0.00 | 0.00 | 0.00 |
| $T2\text{-}NC_4 =$ | 0.00 | 16.57 | 2.38 | 0.00 | 0.00 | 0.00 |
| 1,3BD | 0.00 | 0.15 | 0.00 | 0.00 | 0.00 | 0.00 |
| $NC_5$ | 0.00 | 0.00 | 0.00 | 0.00 | 1.10 | 0.00 |
| $IC_5$ | 0.00 | 0.00 | 0.00 | 0.00 | 0.05 | 0.00 |
| C5= | 0.00 | 0.00 | 0.26 | 0.00 | 0.00 | 0.00 |
| C6= | 0.00 | 0.00 | 0.10 | 0.00 | 0.00 | 0.00 |
| C6 | 0.00 | 0.00 | 0.00 | 0.00 | 0.46 | 0.00 |
| C7= | 0.00 | 0.00 | 0.26 | 0.00 | 0.00 | 0.00 |
| C7 | 0.00 | 0.00 | 0.00 | 0.00 | 1.14 | 0.00 |
| C8= | 0.00 | 0.00 | 13.34 | 0.00 | 0.00 | 0.00 |
| C8 | 0.00 | 0.00 | 0.00 | 0.00 | 58.41 | 0.00 |
| C9= | 0.00 | 0.00 | 0.28 | 0.00 | 0.00 | 0.00 |
| C9 | 0.00 | 0.00 | 0.00 | 0.00 | 1.22 | 0.00 |
| C10= | 0.00 | 0.00 | 0.06 | 0.00 | 0.00 | 0.00 |
| C10 | 0.00 | 0.00 | 0.00 | 0.00 | 0.28 | 0.00 |
| C12= | 0.00 | 0.00 | 0.94 | 0.00 | 0.00 | 0.00 |
| C12 | 0.00 | 0.00 | 0.00 | 0.00 | 4.12 | 0.00 |
| PX | 0.00 | 0.00 | 0.03 | 0.00 | 0.11 | 0.00 |
| Heavies | 0.00 | 0.00 | 0.06 | 0.00 | 0.27 | 0.00 |

Separator 22 withdraws a hydrogen stream containing about 85 mol % hydrogen and 10 mol % $C_3$ and lighter hydrocarbons from the dehydrogenation zone effluent via line 24. The remainder of the dehydrogenation zone effluent is combined with an olefin feed having the composition given in Table 2 for line 32. The combined isobutene and olefin feed enters the oligomerization reactors at a temperature of about 300° F. and a pressure of about 500 psig.

Aliquot portions of the oligomerization zone feed stream pass in parallel through oligomerization reactors containing an SPA catalyst. The feed fractions contact the catalyst at an LHSV of about 4. Temperature rise in the oligomerization reaction zones is minimized by the high concentration of unreactive isobutane as well as a staged addition of quench medium to the reaction zones. The effluent from the oligomerization zone has the composition given in Table 2 for line 34.

The effluent from the oligomerization passes into the debutanizer column 16. Lighter components comprising primarily $C_4$ and lower boiling components pass upwardly through a bed of oligomerization catalyst comprising a Y zeolite that oligomerizes a portion of the $C_4$ olefins and paraffins. The remainder of the lighter components pass through a bed of saturation catalyst comprising nickel or palladium on a suitable support. The previously described recycle stream 18 is withdrawn from the column above the bed of saturation catalyst and a net overhead stream having the composition given in Table 2 for line 41 is withdrawn from the top of the column. The column also delivers a side cut stream 74 comprises mainly isobutane and having the composition given in Table 2.

A hydrotreater feed is withdrawn from a lower portion of the debutanizer column and mixed with a recycle hydrogen. The hydrogen addition comprises primarily 85 mol % purity hydrogen from the dehydrogenation zone separator. The feed enters the saturation zone at a temperature of about 500° F. and a pressure of about 400 psig. The saturation zone consists of two serial hydrotreating reactors that contact the feed at an LHSV of about 10 with a saturation catalyst comprising nickel and molybdenum on an alumina base. Quench is intermixed with the intermediary effluent between the hydrotreating reaction zones. After separation for recovery of quench materials and recycle hydrogen, the effluent from the hydrotreating reactors has the composition given in Table 2 for line 68 and reenters the lower portion of the debutanizer.

What is claimed is:

1. A process for the production of an oligomerization zone product from a feedstream comprising isobutane, said process comprising:
    a) passing a dehydrogenation feedstream comprising isobutane and a recycle stream comprising saturated $C_4$ hydrocarbons to a dehydrogenation zone and contacting said feedstream in said dehydrogenation zone with a dehydrogenation catalyst at dehydrogenation conditions to produce a dehydrogenation zone effluent comprising isobutene and hydrogen;
    b) passing at least a portion of said dehydrogenation zone effluent to an oligomerization zone to supply at least a portion of an oligomerization zone feed and contacting said oligomerization zone feed with a solid oligomerization catalyst at oligomerization conditions including a temperature of 200° F. to 500° F., a pressure of 100 psig to 1500 psig, and an LHSV of 0.8 to 5 to recover an oligomerization effluent comprising $C_7$ and heavier oligomers and unconverted isobutene;
    c) passing at least a portion of said oligomerization zone effluent stream to a distillation column and separating $C_4$ and lighter hydrocarbons from said $C_7$ and heavier oligomers;
    d) passing said $C_4$ and lighter hydrocarbons upwardly through said column and into contact with a bed of saturation catalyst in a column saturation zone to saturate said $C_4$ and lighter hydrocarbons and produce said recycle stream comprising $C_4$ saturated hydrocarbons in an upper portion of said column;
    e) recycling the saturated $C_4$ recycle stream from said column to said dehydrogenation zone; and,
    f) withdrawing an oligomerized stream from a lower section of said column.

2. The process of claim 1 wherein at least a portion of said oligomerized stream from said column passes into a saturation zone along with hydrogen recovered from said dehydrogenation zone effluent and contacts a saturation catalyst at saturation conditions to saturate olefins in said oligomerized stream and produce a saturated stream.

3. The process of claim 2 wherein at least a portion of said saturated stream is passed to a separation zone and a net bottoms stream comprising $C_7$ and heavier paraffins is recovered from said separation zone.

4. The process of claim 1 wherein an oligomerization zone feed comprising $C_4$ olefins is passed to said oligomerization zone with said dehydrogenation zone effluent stream.

5. The process of claim 1 wherein said distillation column contains a bed of alkylation catalyst below said column saturation zone and said $C_4$ and lighter hydrocarbons pass upwardly through said bed of alkylation catalyst at alkylation conditions before entering said column saturation zone.

6. The process of claim 5 wherein said bed of alkylation catalyst is selected from the group consisting of sulfated alumina, beta zeolite, Y zeolite, or ion exchange resins.

7. The process of claim 2 wherein said oligomerized stream is recovered from said distillation column at an intermediate tray location, said saturated stream enters a separator column that recovers hydrogen for recycle to said saturation zone, and the remainder of said saturated stream is returned to said distillation column at a tray location below said intermediate tray location.

8. The process of claim 1 wherein said saturated $C_4$ recycle stream is withdrawn from said distillation column as a sidecut liquid recycle stream.

9. The process of claim 1 wherein said distillation column contains a bed of oligomerization catalyst below said column saturation zone and said $C_4$ and lighter hydrocarbons pass upwardly through said bed of oligomerization catalyst at oligomerization conditions before entering said column saturation zone.

10. The process of claim 1 wherein a first portion of the oligomerized stream comprising $C_7$ to $C_{10}$ olefins is withdrawn from the lower section of the distillation column at an intermediate tray location and a second portion of the oligomerized stream comprising $C_{11}$ and higher molecular weight olefins is withdrawn from the distillation column below the withdrawal point of the first portion of the oligomerized stream.

11. A process for the production of a motor fuel product from a first isobutane-containing input stream and a second input stream comprising olefins, said process comprising:
    a) passing at least a portion of said first input stream comprising isobutane and a $C_4$ recycle stream to a dehydrogenation zone and contacting said feedstream in said dehydrogenation zone with a dehydrogenation catalyst at dehydrogenation conditions to produce a dehydrogenation zone effluent comprising isobutene and hydrogen;
    b) separating hydrogen from said dehydrogenation effluent to produce a first hydrogen stream and a separated dehydrogenation effluent;
    c) passing at least a portion of said separated dehydrogenation effluent and said second input stream to an oligomerization zone and contacting said separated dehydrogenation effluent and said second input stream with a solid oligomerization catalyst at oligomerization conditions including a temperature of 200° F. to 500° F., a pressure of 100 psig to 1500 psig, and an LHSV of 0.8 to 5 to recover an oligomerization effluent comprising $C_8$ and higher oligomers and unconverted isobutene;
    d) passing said oligomerization zone effluent stream to a distillation column and separating $C_4$ and lighter hydrocarbons from said $C_8$ and heavier oligomers;
    e) passing said $C_4$ and lighter hydrocarbons upwardly through said column and first into contact with a bed of alkylation catalyst at alkylation conditions to alkylate $C_4$ olefins and produce $C_8$ and heavier oligomers that pass downwardly from said bed of alkylation catalyst;

f) passing $C_4$ and lighter hydrocarbons from said bed of alkylation catalyst upwardly in said column to a bed of saturation catalyst in a column saturation zone to saturate said $C_4$ and lighter hydrocarbons and to produce said $C_4$ recycle stream comprising saturated hydrocarbons in an upper portion of said column;

g) recycling said saturated $C_4$ recycle stream from said column to said dehydrogenation zone;

h) recovering an oligomerized stream comprising $C_8$ and heavier olefins from said distillation column and passing said oligomerized stream and said first hydrogen stream to a saturation zone and into contact with a saturation catalyst at saturation conditions to saturate olefins in said oligomerized stream and to produce a saturated stream;

i) separating a second hydrogen stream from said saturated stream for return to said saturation zone and returning the remainder of said saturated stream to said distillation column; and, j) recovering a net bottoms stream comprising said motor fuel product from said distillation column.

12. The process of claim 11 wherein the saturation zone comprises a hydrotreater.

13. The process of claim 11 wherein said second input stream contains at least 30 wt % isobutene.

14. The process of claim 11 wherein said distillation column comprises a deisobutanizer.

15. The process of claim 11 wherein said oligomerization zone comprises multiple beds of a solid phosphoric acid catalyst.

16. The process of claim 11 wherein said saturation zone comprises at least two beds of hydrotreating catalyst.

17. The process of claim 11 wherein a light gas stream comprising a majority of C3 and lighter hydrocarbons is withdrawn overhead from said distillation column.

18. The process of claim 11 wherein said second input stream comprises at least 20 wt % normal butenes.

19. The process of claim 11 wherein said bed of alkylation catalyst is selected from the group consisting of sulfated alumina, beta zeolite, Y zeolite, or ion exchange resins.

20. The process of claim 11 wherein said oligomerized stream is recovered from said distillation column at an intermediate tray location and said remainder of said saturated stream enters said distillation column at tray location below said intermediate tray location.

21. The process of claim 11 wherein said saturated $C_4$ recycle stream is withdrawn from said distillation column as liquid sidecut stream.

* * * * *